United States Patent [19]

Billingham et al.

[11] Patent Number: 5,700,403
[45] Date of Patent: Dec. 23, 1997

[54] DISTILLATION COLUMN EMPLOYING STRUCTURED PACKING WHICH REDUCES WALL FLOW

[75] Inventors: John Fredric Billingham, Tonawanda; Michael James Lockett, Grand Island, both of N.Y.

[73] Assignee: Praxair Technology, Inc., Danbury, Conn.

[21] Appl. No.: 590,663

[22] Filed: Jan. 24, 1996

[51] Int. Cl.⁶ ............................................. B01F 3/04
[52] U.S. Cl. ............................................. 261/112.2
[58] Field of Search ............................... 261/112.2

[56] References Cited

U.S. PATENT DOCUMENTS

| | | | |
|---|---|---|---|
| 3,599,943 | 8/1971 | Munters | 261/95 |
| 4,732,713 | 3/1988 | Korsell | 261/112.2 |
| 4,929,399 | 5/1990 | Lockett et al. | 261/112.2 |
| 5,132,056 | 7/1992 | Lockett et al. | 261/112.2 |
| 5,154,859 | 10/1992 | Bosquain et al. | 261/112.2 |
| 5,224,351 | 7/1993 | Jeannot et al. | 62/36 |
| 5,262,095 | 11/1993 | Bosquain et al. | 261/112.2 |
| 5,441,793 | 8/1995 | Suess | 261/112.2 |

Primary Examiner—Tim R. Miles
Attorney, Agent, or Firm—Stanley Ktorides

[57] ABSTRACT

A heat and/or mass exchange structure which includes a shell having an outer vertical wall with an interior surface, a plurality of first corrugated packing sheets having an outer edge that is spaced away from the interior surface of the shell, and a plurality of second corrugated packing sheets positioned within the shell and sandwiched between a pair of the first corrugated packing sheets.

6 Claims, 4 Drawing Sheets

10 BRICKS/LAYER

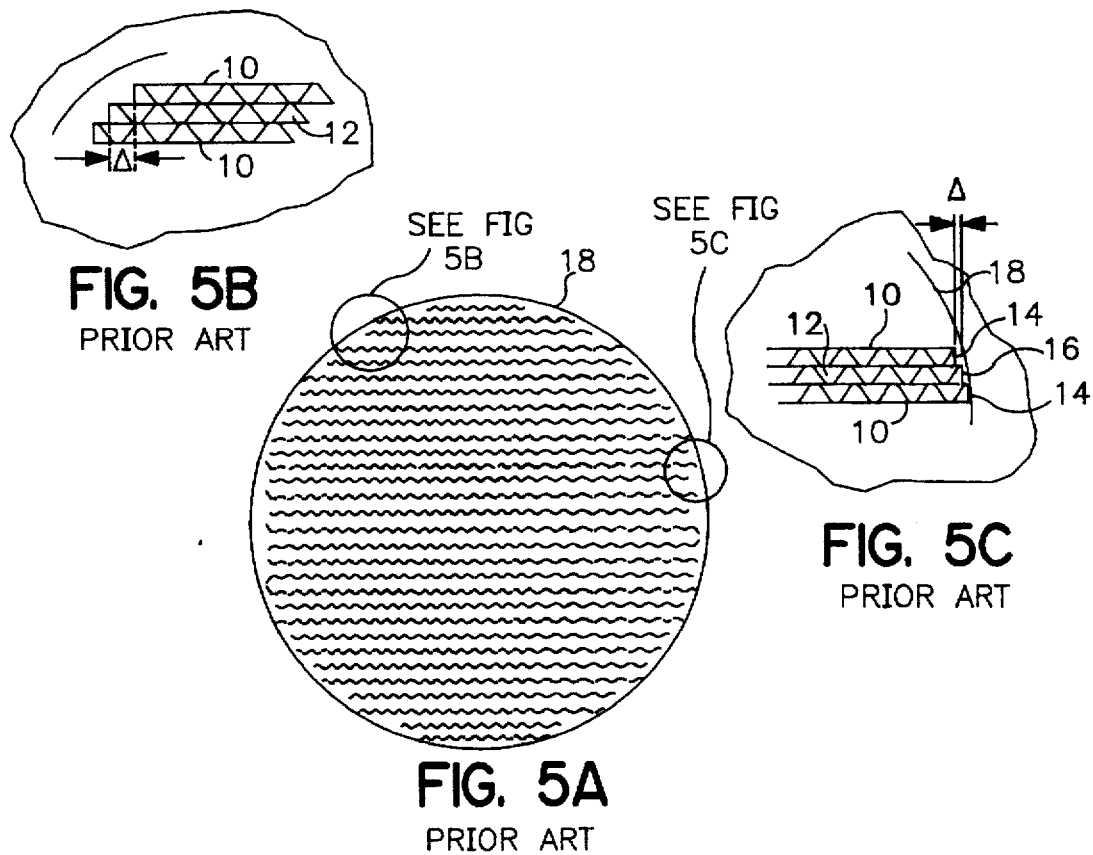
FIG. 5B
PRIOR ART
FIG. 5C
PRIOR ART
FIG. 5A
PRIOR ART
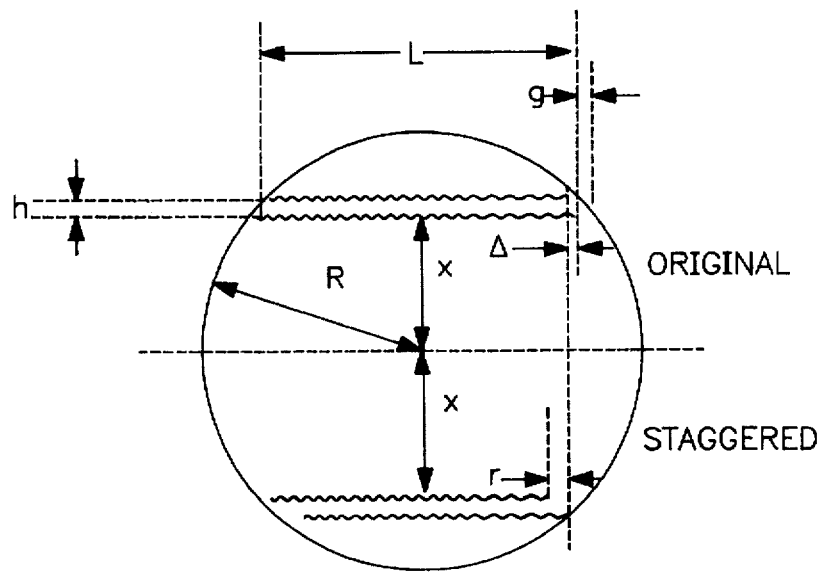
FIG. 8

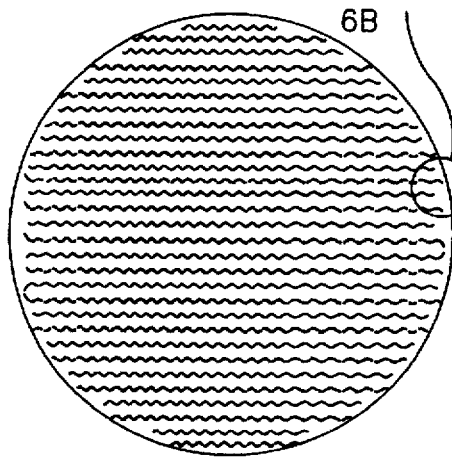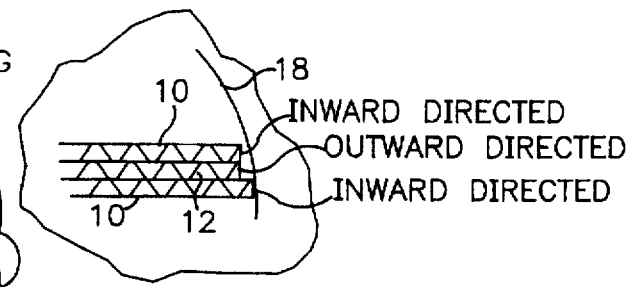
FIG. 6    FIG. 6B
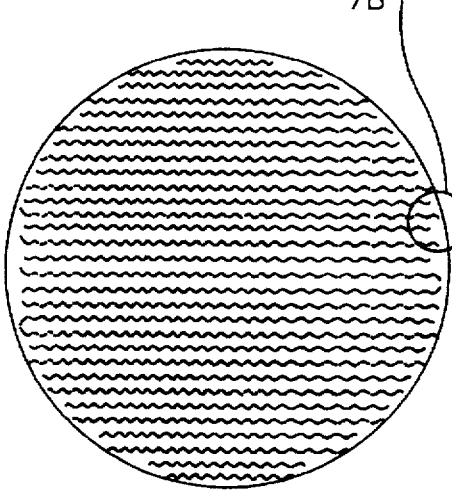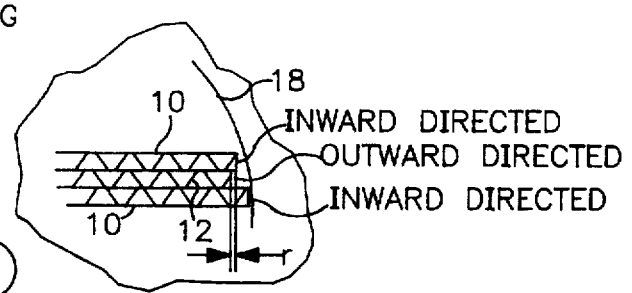
FIG. 7    FIG. 7B

DISTILLATION COLUMN EMPLOYING STRUCTURED PACKING WHICH REDUCES WALL FLOW

FIELD OF THE INVENTION

This invention relates to distillation columns and, more particularly, to structured packing for such distillation columns which substantially reduces column wall flow.

BACKGROUND OF THE INVENTION

Distillation columns are used for a wide variety of separations in industry. One area of application of distillation columns is in cryogenic air separation systems for the production of oxygen and nitrogen. In a distillation column, as the liquid and vapor flow past each other, both mass and heat are exchanged. In a cryogenic air separation facility, the liquid becomes warmer and more rich in oxygen as it flows downward, whereas the upward flowing gas becomes both colder and more nitrogen rich. Over the past decade, structured packing has been employed in such distillation columns due to its low pressure drop and high mass transfer efficiency when compared to more traditional distillation column internals, such as trays.

As shown in FIG. 1, many structured packings employ vertically oriented corrugated packing sheets 10 and 12, wherein the corrugations are arranged at an angle to the vertical. Each packing sheet is positioned such that its corrugation direction is reversed from the corrugation direction of its neighboring packing sheet. A vertical edge of each packing sheet is distinguished by the motion it imparts to liquid flowing on the respective edge. Thus, packing sheet 10 includes a vertical edge 14 which is characterized by the fact that liquid flow directed downwards along edge 14 is directed inwardly and away from a wall surface adjacent thereto. Similarly, packing sheet 12 includes a vertical edge 16 whose corrugations direct liquid flow in an outward direction towards an adjacent wall surface.

The above can better be understood by referring to FIG. 2 wherein a side view of packing sheet 12 is shown adjacent to a distillation column wall 18. Liquid is introduced in the direction indicated by arrow 20 and percolates downward as a film on the corrugated sheets with a vapor flowing upwards in channels formed between the sheets. A certain fraction of the downward liquid flow reaches vertical edge 16 of packing sheet 12 and travels downward along this edge. Liquid is also transferred to the inner surface of distillation column wall 18 and travels downwardly along this edge. The resulting wall flow bypasses the packing which both substantially reduces the efficiency of the distillation column and contributes to a maldistribution of the liquid within the column.

In FIG. 3, a packed column section 22 is illustrated without an encompassing shell structure. The packing sheets are installed in bundles 24 that are arranged in layers, each layer generally between 6 and 12 inches in height. Adjacent layers 26, 28 and 30 are rotated around a vertical axis to enhance mixing of the downwardly flowing liquid which is being distilled against an upwardly flowing vapor. In small columns, each layer 26, 28, 30 may be comprised of a single "brick" of packing sheets formed by fixing individual packing sheets together using rods that pierce all of the sheets, or by using bands that fit around the circumference of each brick. In large columns, each layer may be made from a plurality of bricks of packing sheets that fit together to fill the cross section of the containing vessel.

In FIG. 4, a set of 10 bricks comprises a single layer of the packed column section. The corrugation pattern within each brick may be sawtoothed or sinusoidal or some other recurring shape. The individual packing sheets touch each other at contact points along the peaks and valleys of the corrugations.

The cross-sectional area of a distillation column is dictated primarily by the vapor and liquid flow rates and densities. Typically, columns are designed to operate at 80%–90% of the flow rate at the flood point, for the packing in question. The flood point is the maximum vapor flow rate at a fixed liquid flow rate at which the column is operable. Physically, the flood point occurs when the vapor loading is such that the liquid can no longer flow countercurrently under gravity and against the vapor.

Vapor maldistribution is generally a minor problem in distillation columns since the vapor is the continuous phase and is able to equalize any radial flow variations through pressure equalization. By contrast, liquid maldistribution is a greater problem since the degree of radial mixing is less. For this reason, significant efforts have been put into designing the liquid distribution structures that are positioned above the packing and deliver the liquid to the distillation column. However, it is known that even with good initial liquid distribution, a point is reached on moving down the distillation column where performance begins to deteriorate. For this reason, packed column sections are generally limited to approximately 15 layers of packing. If a given column requires more than 15 layers, the column is split into two or more sections, with means for collection and redistribution of liquid positioned between them. Such structures involve additional capital cost and create increased column height. The added height is a particularly severe penalty in the air separation industry, due to the need for a cold-box and insulation to encase the column and thus reduce heat leakage.

A reduction in performance with height occurs in such distillation columns and is due to the packing inducing maldistribution of the downward liquid flow. This phenomenon is generally attributed to wall flow which is the liquid that flows down the interior of the column shell, effectively bypassing the packing. It is typically countered in the prior art through use of wall wipers which are a series of tabs which contact the inner surface of the column shell and redirect wall flow back into the packing.

As shown in FIG. 5, the prior art has arranged packing sheets by sandwiching each outwardly directed packing sheet 12 between adjacent inwardly directed packing sheets 10. The packing sheets are arranged so that their respective vertical edges 14 and 16 are arranged to approximate the curvature of distillation column wall 18, while being separated from the interior surface thereof. The difficulty with an arrangement such as shown in FIG. 5 is that only one side of outwardly directed packing sheet 12, at its edge, is contacted by an adjacent inwardly directed sheet 10. Thus, there are no contact points between inwardly directed packing sheet 10 and outwardly directed packing sheet 12 for a distance Δ which varies in size in accordance with the arrangement of the packing sheets and the diameter of the distillation column. The exposed areas exhibit a region wherein liquid flow has an unimpeded outlet towards the inner surface of wall 18. In addition, this flow represents a maldistribution.

As can be seen from the expanded areas in FIG. 5, the exposed area is a minimum for the longest packing sheets and a maximum for the shortest packing sheets.

Besides wall wipers, the prior art has described a number of techniques for attempting to decrease liquid maldistribution.

U.S. Pat. No. 3,599,943 to Munters illustrates use of cross-corrugated packing sheets wherein the folds of the corrugations have vertical cuts near the lowermost edges thereof. Such cuts cause liquid flowing along a fold to change flow direction prior to the liquid reaching an edge.

U.S. Pat. No. 5,262,095 to Bosquain et al and U.S. Pat. No. 5,224,351 to Jeannot et al both include deformations at outward edges of each packing sheet to create an obstacle to liquid flow. Such deformations cause outwardly directed liquid to be redirected in an inward direction.

The innovations described in the aforesaid patents require additional processing of the individual packing sheets with a resulting cost increase.

It is therefore an object of this invention, to provide structured packing for a distillation column which reduces the rate at which liquid maldistribution develops.

It is another object of this invention to provide improved structured packing for a distillation column which requires minimum additional capital cost and little added manufacturing complexity.

It is a further object of this invention to provide improved structured packing for a distillation column that reduces wall flow without requiring substantial structural modification to the corrugated packing sheets.

SUMMARY OF THE INVENTION

This invention comprises a heat and mass exchange structure which includes a shell having an outer vertical wall with an interior surface. A plurality of first corrugated packing sheets include corrugations angled to carry a downwardly flowing liquid away from the interior surface of the shell. Each first corrugated packing sheet has an outer edge that is spaced away from the interior surface of the shell. A plurality of second corrugated packing sheets are positioned within the shell and each is sandwiched between a pair of the first corrugated packing sheets. Each second corrugated packing sheet includes corrugations angled to carry downwardly flowing liquid toward the interior surface of the vertical wall of the shell. Each second corrugated packing sheet has an outer edge which is spaced no closer to the interior surface of the vertical wall of the shell than the outer edge of either of the pair of first corrugated packing sheets which sandwich the second corrugated packing sheet.

BRIEF DESCRIPTION OF THE DRAWINGS

Other objects, features and advantages will occur to those skilled in the art from the following description of a preferred embodiment of the invention and the accompanying drawings, in which:

FIG. 5 illustrates a plan view of a single brick/layer in a prior art distillation column.

FIG. 6 illustrates a plan view of a single brick/layer which incorporates the invention.

FIG. 7 illustrates a plan view of a single brick/layer which incorporates a further embodiment of the invention.

FIG. 8 illustrates parameters that are used in arriving at designs for packing sheet arrangements which incorporate the invention.

DETAILED DESCRIPTION OF THE PREFERRED EMBODIMENTS

Figure 1:
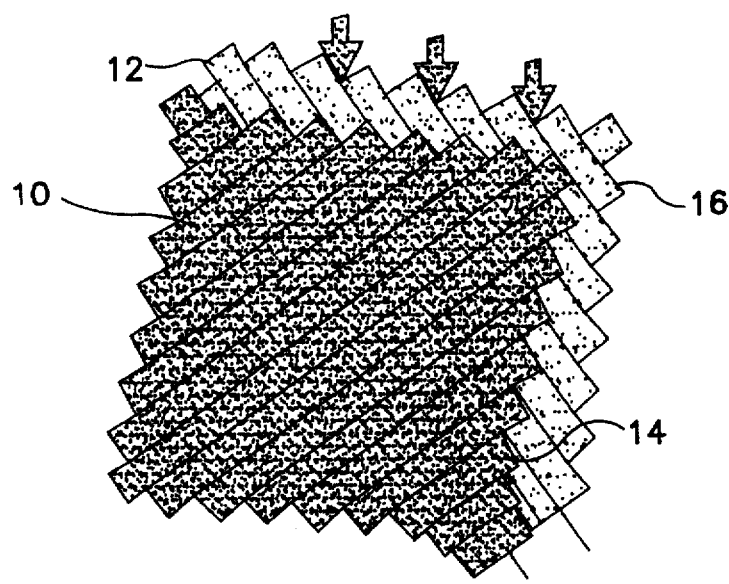
FIG. 1 illustrates a pair of corrugated packing sheets exhibiting both outwardly directed and inwardly directed flow directions for liquid passing thereover.
Figure 2:
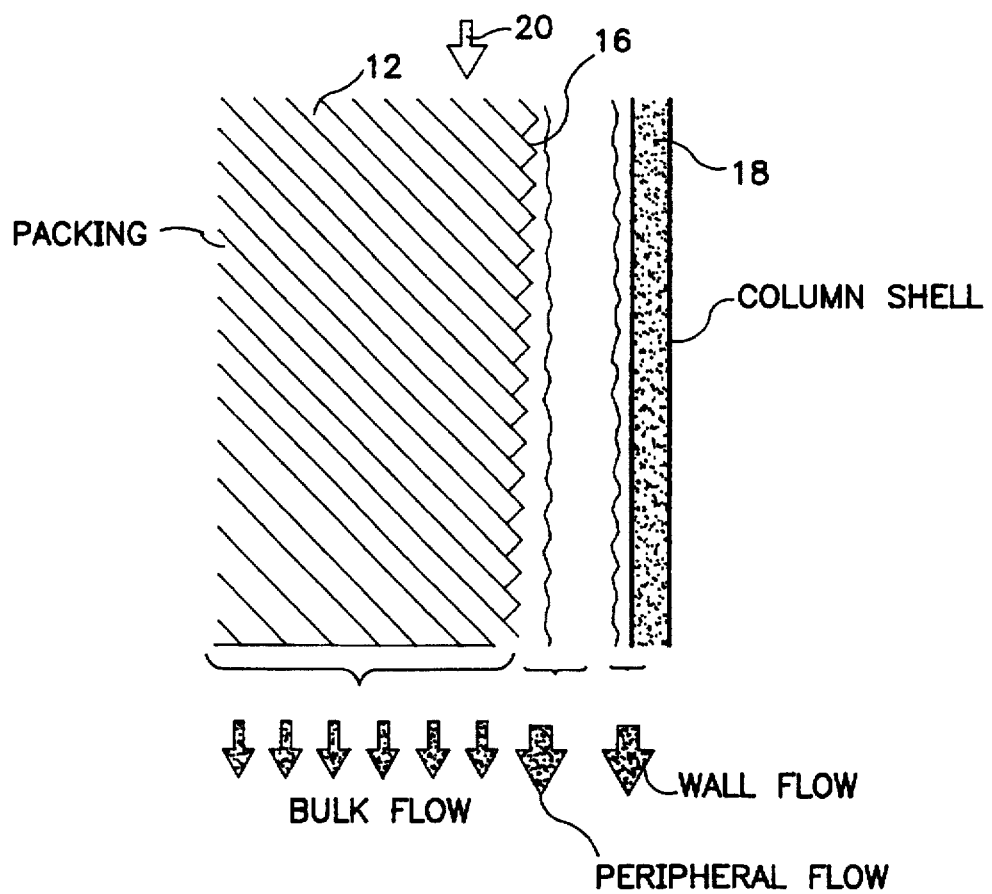
FIG. 2 is a schematic of an outwardly directed corrugated packing sheet and an adjacent distillation column wall.

The invention arranges packing sheets such that at every vertical edge, a packing sheet with an outwardly directed corrugation is surrounded on both sides by packing sheets with inwardly directed corrugations. More specifically, inwardly directed packing sheets are arranged about each outwardly directed packing sheet such that there is no delta distance where the outwardly directed packing sheet is exposed. By this arrangement, liquid at the vertical edge of any outwardly directed packing sheet has an improved opportunity to be transferred back into the bulk of the packing.

The above described arrangement is most beneficial in circular columns where adjacent packing sheets are cut to different lengths in order to best approximate the circular cross-section. In the preferred embodiment, outwardly directed packing sheets have their vertical edges recessed a distance of approximately one-half the corrugation crimp height behind the shorter of neighboring inwardly directed packing sheets. It is to be understood that any outwardly directed packing sheet at one extremity, which extends entirely across a circular column, is inwardly directed at its opposite extremity. A similar reversal occurs for an outwardly directed packing sheet. Accordingly, the edge relationships to be hereafter defined for such sheets are reversed at their opposite extremities if they extend across the circular column.

Referring to FIG. 6, an arrangement of packing sheets is illustrated in accordance with the invention. The lengths of outwardly directed packing sheets 12 are shortened with respect to the prior art arrangement. Thus, each outwardly directed packing sheet 12 extends no further outward than the vertical surface of the shortest adjoining inwardly directed packing sheet 10. By this arrangement, each outwardly directed packing sheet 12 has contact points along its entire outer vertical length for transfer of liquid to inwardly directed packing sheets 10. This reduces the amount of liquid that is enabled to pass into contact with the interior surface of shell wall 18 or that builds up on the packing periphery.

Referring to FIG. 7, a further embodiment of the invention is illustrated wherein each outwardly directed packing sheet 12 is recessed inwardly from each inwardly directed packing sheet 10 that adjoins it. This arrangement assures, with even greater certainty, that liquid does not accumulate at the outer vertical edge of each outwardly directed packing sheet 12 and also decreases the likelihood of liquid detaching from outwardly directed packing sheet 12 and flowing down column shell wall 18. A preferred inset distance of each outwardly directed packing sheet 12 is approximately one-half the corrugation height. The inset is measured from the edge of the shorter inwardly directed sheet 10.

The arrangements shown in FIGS. 6 and 7 are particularly attractive in that they are applicable to any type of structured packing that is manufactured from packing sheets placed side by side. Such packing sheets require no special tooling or increased capital expense, yet enable longer beds to be used more effectively. The optimal arrangement recesses each outwardly directed packing sheet a distance less than the crimp height behind the shorter of its neighboring inwardly directed packing sheets.

Figure 3:
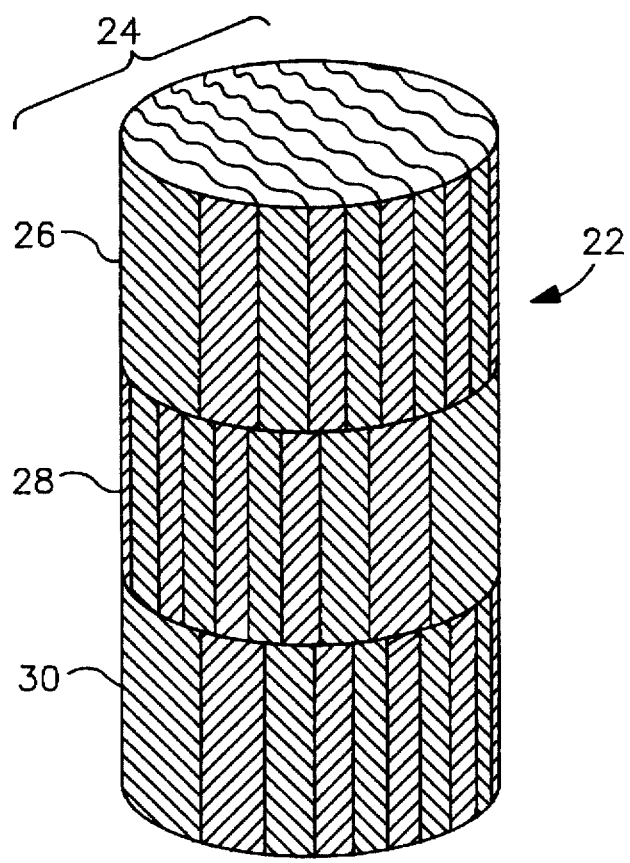
FIG. 3 illustrates the structure of a packed section of a distillation column employing three layers of corrugated packing sheets.
Figure 4:
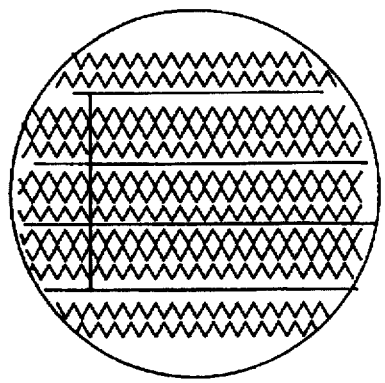
FIG. 4 illustrates a layer of packing sheets, in cross section, comprising a plurality of bricks of packing sheets.

Structured packings are generally textured, crimped, then cut into required lengths before being placed in a form that is the shape of a required "brick". For small diameter columns (generally less than 3 ft.), the sheets may extend the entire chordal length as shown in FIG. 3. For such an arrangement, the length of any given sheet is related to the perpendicular distance from the column axis by the following relationship (see FIG. 8 for nomenclature):

$$L=2[(R-g)^2-x^2]^{0.5}$$

where: g is the gap between the packing and the wall (in.),
x is the perpendicular distance from the centerline (in.),
R is the internal radius of the shell (in.),
L is the length of the sheet (in.).

The exposed length, $\Delta$, associated with this sheet located a distance of x from the center line is calculated from;

$$\Delta=[(R-g)^2-x^2]^{0.5}-[(R-g)^2-(x+h)^2]^{0.5}$$

where: h is the crimp height (in.)

The total length that the sheet needs to be shortened is then $\Delta$ plus the recess, r (FIG. 8). For example, given a 4 ft. internal diameter, a crimp height and wall gap of 0.2 and 0.5 in., respectively, some lengths of sheets in the original arrangement together with the amount they need to be reduced are given in Table 1. The table assumes a recess of 1/8 in.

TABLE 1

REDUCTION IN SHEET LENGTH FOR CHORDAL ELEMENTS

| x (in) | L (in) | $\Delta$ + r (in) |
|---|---|---|
| 4 | 46.31 | 0.16 |
| 9 | 44.19 | 0.2 |
| 12 | 40.41 | 0.25 |
| 16 | 34.42 | 0.31 |
| 20 | 24.68 | 0.46 |

For larger diameter columns, single bricks often do not extend across a full layer of a column but instead are made up of several bricks. In such cases, only those bricks that contain an edge at the column wall need to be modified. For no recess, the invention is easily practiced by simply cutting a packing sheet with outwardly directed corrugation angles to the same length as the shorter of its neighbors.

The building of a brick from individual packing sheets is a little more complicated. Using the prior art arrangement, packing sheets are usually stacked into forms that are the shape of the brick and are usually held together by a metal rod which is driven through the packing. In the arrangement according to the invention, more care is required to ensure that the sheets are positioned correctly, since one edge will not contact the form. This may be accomplished by fixing sheets together two at a time with the correct alignment before placement into the form. The attachment can be a nail or a readily removable peg. Alternatively, for bricks with one flat edge such as in larger columns, the sheets can be stacked vertically so that they will automatically align correctly. An alternative is to produce forms with edges that undulate to keep the packing in the correct alignment.

One drawback of the arrangement in accordance with the invention is the reduced coverage of the cross-sectional area of the column by the packing due to the shortened lengths of its sheets. The effectiveness of the approximation to a circle, when using corrugated sheets, improves with decreasing crimp height. The arrangement in accordance with the invention effectively produces a fit to the circle equivalent to that of a packing with twice the crimp height. The fractional loss of area coverage, $\Delta A$, is equivalent to the loss in total length of packing sheets. For an arrangement such as that shown in FIG. 6, with zero recess r, the fractional effective loss in coverage is approximated by;

$$\Delta A = 2h/\pi R$$

As an example, air separation packings are typically used with h=0.20". The fractional loss in coverage is thus 0.01, 0.005 and 0.003 for a 2, 4 and 8 ft column respectively. This is considered to be a negligible amount in terms of loss of interfacial area but may be more significant in terms of vapor bypassing. This occurs because, compared to the rest of the packing, less resistance to flow is offered in the open space between the edge of the packing and the column shell resulting from the shortening of the packing sheets. The problem is encountered in prior art designs due to the presence of a wall gap. It is solved by the use of wall wipers which have various designs, but typically consist of a foil or gauze girdle that wraps around the packing and a series of tabs that flare out from the packing and contact the column shell.

Similarly, the problem of vapor bypassing resulting from the invention can be eliminated through the use of wall wipers that encroach into the space vacated by the shortened sheet.

The magnitude of this may be placed in perspective by noting that the column fit of a 500 m²/m³ specific surface area packing designed according to the invention as shown in FIG. 7 is similar to that obtained with a packing of half the specific surface area, namely 250 m²/m³. Applicants are aware of no reported loss in performance of conventionally manufactured packing having a specific surface area of 250 m²/m³, when compared with packing having a specific surface area of over 500 m²/m³, resulting from vapor bypassing along the gap between the packing and the wall.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A heat and/or mass exchange structure comprising:

a shell including an outer vertical wall having an interior surface said shell containing a packing arrangement comprising:

a plurality of first corrugated heat and/or mass transfer sheets having corrugations angled to as to carry downward flowing liquid towards an interior region of said packing arrangement and away from an external periphery thereof, said external periphery being spaced away from said interior surface; and a second corrugated heat and/or mass transfer sheet sandwiched between each pair of said first corrugated heat and/or mass transfer sheets and having corrugations angled so as to carry downward flowing fluid towards said external periphery, said second heat and/or mass transfer sheet having an outer edge which is spaced further away from said external periphery than co-located outer edges of said pair of said first corrugated heat and/or mass transfer sheets which sandwich said second corrugated heat and/or mass transfer sheet so as to be recessed from both said co-located outer edges.

2. The heat and/or mass exchange structure as recited in claim 1 wherein each said second corrugated heat and/or mass transfer sheet has a corrugation height h and said outer edge thereof is spaced further away from said external periphery than said outer edges of either of said pair of first corrugated sheets which sandwich said second corrugated heat and/or mass transfer sheet, by a distance r where $0 \leq r \leq h$.

3. The heat and/or mass exchange structure as recited in claim 2, wherein r is approximately h/2.

4. A packing arrangement for a distillation column, comprising:

a plurality of first corrugated heat and/or mass transfer sheets having corrugations angled so as to carry downward flowing liquid towards an interior region of said packing arrangement and away from an external periphery thereof and further having an outer edge; and a second corrugated heat and/or mass transfer sheet sandwiched between each pair of said first corrugated heat and/or mass transfer sheets and having corrugations angled so as to carry downward flowing fluid towards said external periphery, said second heat and/or mass transfer sheet having an outer edge which is spaced further away from said external periphery than co-located outer edges of either of said pair of said first corrugated heat and/or mass transfer sheets which sandwich said second corrugated heat and/or mass transfer sheet so as to be recessed from both said co-located outer edges.

5. The packing arrangement as recited in claim 4, wherein each said second corrugated heat and/or mass transfer sheet has a corrugation height h and said outer edge thereof is spaced further away from said external periphery than outer edges of either of said pair of first corrugated sheets which sandwich said second corrugated heat and/or mass transfer sheet, by a distance r where $0 \leq r \leq h$.

6. The packing arrangement as recited in claim 5, wherein r is approximately h/2.

* * * * *